United States Patent [19]

Thau

[11] Patent Number: 4,981,677
[45] Date of Patent: Jan. 1, 1991

[54] PETROLATUM-CONTAINING AEROSOL FOAM CONCENTRATE

[75] Inventor: Paul Thau, Berkeley Heights, N.J.

[73] Assignee: L'Oreal, Paris, France

[21] Appl. No.: 271,506

[22] Filed: Nov. 15, 1988

Related U.S. Application Data

[63] Continuation-in-part of Ser. No. 100,093, Sep. 23, 1987, abandoned.

[51] Int. Cl.$^5$ ................................................ A61L 9/04
[52] U.S. Cl. ........................................ 424/45; 424/40; 424/43; 424/44; 424/47
[58] Field of Search ...................... 424/40, 43, 44, 45, 424/47

[56] References Cited

U.S. PATENT DOCUMENTS

| | | | |
|---|---|---|---|
| 3,864,474 | 2/1975 | Gerecht | 514/972 X |
| 3,970,584 | 7/1976 | Hart et al. | 424/45 |
| 4,088,760 | 5/1978 | Benson et al. | 514/177 |
| 4,396,615 | 8/1983 | Petrow et al. | 514/177 |
| 4,806,262 | 2/1989 | Snyder | 252/90 |

Primary Examiner—Merrell C. Cashion, Jr.
Assistant Examiner—P. L. Prater
Attorney, Agent, or Firm—Cushman, Darby & Cushman

[57] ABSTRACT

A skin conditioning composition for application to the skin comprises an oil-in-water emulsion and a propellant packaged under pressure in an aerosol device or controller. The oil-in-water emulsion comprises petrolatum, water and an emulsifier having an HLB of about 6 to 10.

19 Claims, No Drawings

PETROLATUM-CONTAINING AEROSOL FOAM CONCENTRATE

This application is a continuation-in-part of application Ser. No. 100,093, now abandoned filed on Sept. 23, 1987.

BACKGROUND OF THE INVENTION

Solid petrolatum or petroleum jelly, hereinafter referred to as petrolatum, has been widely used as a therapeutic agent for topical applications. This therapeutic agent possesses well known lubricating, softening and skin conditioning characteristics, and many dermatologists have endorsed the use of petrolatum as an effective hydrating agent and skin protectant for patients with dry or scaly skin.

Petrolatum consists of a mixture of hydrocarbons (including mineral oil and microcrystalline hydrocarbon waxes) of such nature that when the melted material is cooled to ordinary room temperatures, it congeals to a translucent, amorphous or jelly-like material.

The U.S. Pharmacopeia (U.S.P.) uses the terms white petrolatum and white petroleum jelly as being the same and describes them as a purified mixture of semi-solid hydrocarbons obtained from petroleum and wholly or nearly decolorized. Petrolatum is further defined as nearly having a melting point range of 38° C. to 60° C. or 100.4° F. to 140° F. and as having a consistency as determined by the U.S.P. official method of not less than 100 and not more than 275. A lesser decolorized grade is described in the National Formulary (N.F.) as a "yellow" grade and as free or nearly free from odor and taste.

Among the many attributes of petrolatum, which make its use in topical applications advantageous are its moisturizing efficacy, water barrier property, water repellency, resistance to being washed off by water, physiological inertness, and chemical inertness and stability.

The chief drawbacks of petrolatum in topical compositions are its greasiness, cosmetic inelegance and the inability to obtain a thin and consistent film over a large area of skin.

In the past, cosmetic compositions containing petrolatum have tried to avoid the drawbacks associated with petrolatum by keeping its concentration low, e.g. below 10% by weight of the total composition, or by adding additives to reduce the composition's greasy feel and appearance. Cosmetic compositions with low concentrations of petrolatum or with additives often do not exhibit all the therapeutic attributes of petrolatum. U.S. Pat. No. 3,852,475, issued Dec. 3, 1974, discloses a petrolatum-containing ointment which incorporates a hydrophobic starch in order to reduce the greasy feel and appearance of the ointment and its resistance to washing. However, the ointment of U.S. Pat. No. 3,852,475 still suffers from cosmetic inelegance and can not be easily spread into a thin film over a large area of skin.

The present invention overcomes the disadvantages associated with petrolatum in cosmetic compositions by providing a composition in the form of a foam. Additionally, the foam produced by the present invention has a substantially consistent foam density from initial dispensing to final dispensing, unlike the presently available cosmetic foams wherein the foam density increases dramatically as the container is emptied. Moreover, the foam of the present invention may be produced from a concentrate having a high petrolatum to emulsifier concentration ratio thereby maintaining the desirable skin-hydrating efficacy of petrolatum.

The present invention relates to a skin conditioning composition for application to the skin, said composition comprising an oil-in-water emulsion and a propellant packaged under pressure in an aerosol device or container under such conditions so as to form a foam having a foam density which changes less than 30 percent from intial dispensing to final dispensing from said aerosol device, said oil-in-water emulsion comprising (a) at least 10 percent by weight of petrolatum, and generally about 10 to about 40 weight percent and preferably about 12.5 to about 35 weight percent, (b) at least 50 weight percent water and generally about 50 to about 80 weight percent and preferably about 55 to about 77 weight percent, and (c) an emulsifier having a hydrophile-lipophile balance value of 6 to 10 and generally present in an amount of about 2 to about 10 weight percent and preferably about 2 to about 5 weight percent, said percentages being based on the total weight of said oil-in-water emulsion.

DETAILED DESCRIPTION OF THE INVENTION

In one embodiment of the present invention there is provided a package for dispensing a foam which comprises:

(a) a pressure-tight container having a valve-controlled opening and a manually-operated valve;

(b) an oil-in-water emulsion useful as a foam-producing aerosol concentrate contained in said container and comprising at least 10% by weight of the total weight of the emulsion of petrolatum, at least 50% by weight of water, and an emulsifier having a Hydrophile-Lipophile Balance value of about 6 to 10; and (c) a propellant contained in said container which is gaseous at room temperature and atmospheric pressure.

Preferably, the emulsion and propellant of the present invention are enclosed in a pressure-tight container. In the most usual form, the container is cylindrical with a concave of flat bottom and a convex top dome with a circular opening fitted with a valve. The container body may be made of metal (such as iron, aluminum, or tin), glass, or plastic. The valve is a standard valve used in the aerosol industry for producing a foam product. The type or design of the container is not critical to the present invention. After reading the present disclosure, it will be evident to those skilled in the art of aerosol dispensers that a variety of containers may be used in the practice of the subject invention. Those containers which are known or would be obvious to a person skilled in the art of aerosol dispensers as workable containers in the practice of the invention are intended to be within the scope of the present disclosure.

The emulsion of the present invention is intended to be a foam-producing aerosol concentrate contained in a container with a propellant, the said emulsion being an oil-in-water emulsion. Oil-in-water emulsions produce foams because the propellant is the internal phase; that is, the propellant vaporizes upon discharge and expands in a continuous aqueous matrix to form a foam. The emulsion comprises petrolatum, water and an emulsifier. The petrolatum may be present in any amount. Preferably, however, the amount of petrolatum is at least 10% by weight of the total weight of the emulsion.

Presently, in the most preferred embodiments, the amount of petrolatum is about 20% by weight of the emulsion. Water may also be present in any amount, but it is preferred that the emulsion contain at least 50% by weight of water. Especially preferred are emulsions having approximately 55 to 77% by weight of water.

A variety of emulsifiers may be used in the emulsion and may consist of a single emulsifying agent or, more commonly, a blend of several emulsifying agents. An emulsifier is a molecule that combines a hydrophilic (water-loving or polar) group with a lipophilic (oil-loving or non-polar) group. Emulsifiers are often classified according to the balance between the size and strength of its hydrophilic group and the size and strength of its lipophilic group. This balance is referred to as the emulsifier's Hydrophile-Lipophile Balance (HLB) value. An emulsifier that is lipophilic in character is assigned a low HLB number (below about 9) and one that is hydrophilic in character is assigned a high HLB number (above about 11). A general discussion of the HLB classification system for emulsifiers can be found in "The HLB System: A Time-Saving Guide to Emulsifier Selection" published in 1984 by ICI Americas, Inc., Wilmington, Del. In general emulsifiers for oil-in-water emulsions have HLB values between 6 and 18. In the practice of the present invention, it is desirable that the emulsifier has an HLB value between 6 and 10, preferably between 7 and 9. The most preferred embodiments of the invention utilize a blend of emulsifying agents wherein the blend has an HLB Value of about 8.

In addition to its HLB value, an emulsifier may be classified by its chemical class. Although emulsifiers of several different chemical classes may be suitable in the practice of the invention, ethoxylated fatty alcohols are presently the preferred class of emulsifiers, especially those with fatty alcohol segments having between 10 and 24 carbon atoms. Ethoxylated fatty alcohols (also referred to as polyoxyethylene alcohols or polyethylene glycol fatty alcohol ethers) are nonionic surfactants prepared by ethoxylation of fatty alcohols with ethylene oxide. A variety of emulsifiers with a broad range of properties may be prepared by varying the fatty alcohol used (lipophile segment) and the degree of polymerization of the polyethylene glycol (hydrophile segment). The preferred emulsifiers comprise a cetyl-, lauryl-, myristyl-, oleyl-, stearyl-, or tridecyl-alcohol moiety and a polyethylene glycol moiety having an average number of ethylene oxide units between 2 and 25.

A blend of steareth-2 and steareth-20, ethoxylated fatty alcohols comprising stearyl-alcohol moieties and polyethylene glycol moieties having 2 and 25 ethylene oxide units, respectively, is presently the most preferred emulsifier.

The amount of emulsifier will depend upon the type of emulsifier used, the amount of petrolatum present and the amount of water present. In the embodiments having 20% by weight petrolatum, 65–70% by weight water and an emulsifier comprising a blend of steareth-2 and steareth-20, the amount of emulsifier is about 2.5% by weight of the total weight of the emulsion.

Although not essential to the invention, it may in some cases be desirable to add small proportions of starch to further improve the cosmetic elegance and reduce the tackiness of the final foam composition. Suitable starches are those which are not easily swelled by water and which will absorb considerable water without forming a paste. Especially useful are hydrophobic starches. A hydrophobic starch is a starch which has been modified to impart thereto hydrophobic groups which render the starch hydrophobic in nature rather than hydrophilic as are conventional non-modified starches.

The most common forms of hydrophobic starches are starch esters containing hydrophobic groups and complex ethers of starch. A specific example of a suitable hydrophobic starch is a commercial product sold under the trade name DRY FLO ®.

DRY FLO ® is an aluminum slat of a low-substituted starch half ester of octenyl succinic acid. It is extremely resistant to wetting by water while retaining the capacity of a starch to absorb water without swelling. This starch is also characterized by its free flowing properties even after absorption of considerable water. Although the amount of hydrophobic starch, such as DRY FLO ® is not critical to the invention, an amount below about 10% weight percent and generally about 1 percent up to about 10 percent, and preferably about 3 weight percent of the total oil-in-water emulsion has been found to be suitable.

It may also be desirable to add a silicone to improve the spreadability of the final product and further improve its cosmetic elegance. It is desirable that the silicone be a volatile silicone, such as cyclomethicone, and be present in an amount below about 10 weight percent of the total emulsion, and generally about 1 percent up to about 10 weight percent.

As is well known to those versed in the art of cosmetics, small proportions of other ingredients may also be added to the emulsion to impart desirable characteristics to the final product. Such ingredients inlcude, but are not limited to, preservatives, stabilizing agents, neutralizing agents, viscosity adjusters, and fragrances.

Generally speaking, the propellant ingredient of the invention is a volatile organic material that exists as a gas at ordinary room temperatures, exists largely as a liquid at elevated pressures practically maintainable in suitable containers, and has a low solubility water. The propellant must be of such nature that it does not destroy the foam or decompose the foam-producing emulsion in the container. Typically, the propellant has a vapor pressure within the range of about 5 to about 200 pounds per square inch gauge, and preferably from about 20 to about 70 pounds per square inch gauge, at 70° F. The propellant may be a mixture of two or more compounds which has a vapor pressure within the desired range, although the individual compounds may have vapor pressures outside the desired range. The water solubility of the propellant or propellant mixture should be such that the propellant exists mainly as a liquid phase undissolved in the emulsion when the two are mixed under pressure sufficient to maintain the propellant in the liquid phase.

Particularly when the final foam product is used to provide a skin-conditioning composition, it may be desirable to avoid the use of propellants that result in a tingling or burning sensation when the composition is applied to the skin. Straight chain, branched chain or cyclic, saturated aliphatic hydrocarbons of suitable vapor pressures, such as propane, butane, isobutane and cyclobutane, are suitable foam-producing propellants that do not cause an undesirable burning sensation. Also usable, particularly in admixtures with other propellants are the saturated, partially but not completely fluorinated substituted aliphatic hydrocarbons of suitable vapor pressure, such as difluoroethane.

The amount of propellant used in the invention is not critical but is determinative of the density of the foam produced. The greater the proportion of propellant, the lower will be the density of the foam. In general, useful foam densities lie in the range of about 0.02 to about 0.20 gram per cc. Desirable foam densities lie in the range between about 0.05 and 0.15 gram per cc. Densities in this preferred range can be obtained by using 5% to about 10% by weight of propellant per total weight of the propellant and emulsion composition. The percentage by weight of propellant required to produce a given foam density varies with the molecular weight of the propellant used. When using a propellant mixture comprising 60% by weight of difluoroethane and 40% by weight of butane or isobutane, the proportion of propellant by weight of the composition ranges from about 5% to about 10% for foam densities of about 0.05 to about 0.15 gram per cc.

The composition is preferably enclosed in a container described hereinabove from which it is propelled as needed by the propellant gas pressure in the head space of the container. As the amount of liquid composition in the container decreases, the concentration of the propellant in the liquid composition drops due to the fact that some of the propellant evaporates to fill the increasing head space. Thus, the density of the foam increases as the contents of the container decreases. The foam density of a foam produced by known aerosols may vary greatly from when the container is full to when the container is substantially empty. Typical variations may be as much as 70%, e.g. from about 0.07 gram per cc as the initial foam density to about 0.12 gram per cc as the final foam density.

Another aspect of the present invention is to provide a method of producing a foam from a aerosol dispenser which comprises dispensing the oil-in-water emulsion described above with a propellant, thereby producing a foam having a substantially consistent foam density from initial dispensing to final dispensing. Preferably, the foam has a foam density which changes by less than 30% from initial dispensing to final dispensing. The method comprises dispensing an oil-in-water emulsion with a propellant under conditions so as to produce a foam, the emulsion comprising at least 10% by weight of petrolatum, at least 50% by weight of water and an emulsifier having a Hydrophile-Lipophile Balance Value of about 6 to 10. Initial dispensing is intended to mean dispensing when the container has about 85%-90% by weight of the total amount of emulsion originally filled into said container. Final dispensing is intended to mean dispensing when the container contains about 15% by weight of the total amount of emulsion originally filled into said container.

The container of the present invention is filled with the desired amounts of emulsion and propellant either separately or simultaneously. The propellant ingredients are preferably introduced under a pressure above their vapor pressure at the prevailing temperature so that the propellant is in liquid form except for the small amount in gaseous form that fills the head space. The composition is mixed in the container by agitation induced by the addition of the ingredients or by shaking by the consumer. Accordingly, the emulsion should have a viscosity which enables it to flow at temperatures and pressures existing in the container. It is desirable that the emulsion has a viscosity between about 1 Pa.s and 15 Pa.s, preferably about 7 Pa.s.

The invention is illustrated in the examples which follow. These examples are set forth to aid in an understanding of the invention but are not intended to, and should not be construed to, limit in any way the invention as set forth in the claims which follow thereafter.

EXAMPLE 1

| Aerosol emulsion concentrate | |
|---|---|
| Ingredients | % by weight of total emulsion |
| Water | 68.55 |
| Petrolatum | 20.00 |
| Cyclomethicone (silicone) | 5.00 |
| Aluminum starch octenylsuccinate (starch) | 3.00 |
| Stearath-2 (emulsifier) | 1.73 |
| Steareth-20 (emulsifier) | 0.58 |
| Imidazolidinyl urea (preservative) | 0.30 |
| Methylparaben (preservative) | 0.20 |
| Propylparaben (preservative) | 0.15 |
| Carbomer 941 (stabilizer) (Crosslinked polyacrylic acid with a polyfunctional group) | 0.12 |
| Triethanolamine (neutralizing agent) | 0.12 |
| Mixture of sodium cetyl-stearyl sulfate (co-emulsifying agent) | 0.10 |
| Cetyl alcohol (viscosity adjuster) | 0.10 |
| Disodium EDTA (stabilizer) | 0.05 |

| Foam-producing aerosol composition | |
|---|---|
| Ingredients | % by weight |
| Aerosol emulsion concentrate | 93-95% |
| Propellant blend (60% difluoroethane - 40% butane) | 5-7% |

EXAMPLE 2

| Aerosol emulsion concentrate | |
|---|---|
| Ingredients | % by weight of total emulsion |
| Water | 68.55 |
| Petrolatum | 20.00 |
| Cyclomethicone (silicone) | 5.00 |
| Aluminum starch octenylsuccinate (starch) | 3.00 |
| Ceteth-2 (emulsifier) | 1.70 |
| Ceteth-20 (emulsifier) | 0.61 |
| Imidazolidinyl urea (preservative) | 0.30 |
| Methylparaben (preservative) | 0.20 |
| Propylparaben (preservative) | 0.15 |
| Carbomer 941 (stabilizer) | 0.12 |
| Triethanolamine (neutralizing agent) | 0.12 |
| Sodium cetearyl sulfate (co-emulsifying agent) | 0.10 |
| Cetyl alcohol (viscosity adjuster) | 0.10 |
| Disodium EDTA (stabilizer) | 0.05 |

| Foam-producing aerosol composition | |
|---|---|
| Ingredients | % by weight |
| Aerosol emulsion concentrate | 93-95% |
| Propellant blend | 5-7% |

EXAMPLE 3

Preparation of aerosol emulsion concentrate of example No. 1

Heat approximately 90 percent of the water to about 70° C. Add Carbomer 941 to the water with moderate agitation and continue to mix until completely dispersed (about one hour). While maintaining 70° C., add the mixture of sodium cetyl-stearyl sulfate, disodium EDTA, and methylparaben.

Combine the petrolatum, steareth-2, steareth-20, propylparaben, and heat to 70° C. with low speed mixing until this phase is melted.

Slowly add the above oil phase to the aqueous phase with high shear agitation (Homo-mixer). After the emulsion forms, add the triethanolamine.

Allow the batch to cool to 50° C. with continued homomixing and then add the imidazolidinyl urea and the remaining water.

At 50° C. or below, add the cyclomethicone and then sprinkle in the aluminum starch octenylsuccinate as the batch cools further. Allow the batch to cool to 30° C. with low speed mixing.

EXAMPLES 4–7

| Aerosol emulsion concentrate | | | | |
|---|---|---|---|---|
| | % by weight of total emulsion | | | |
| Ingredients | Ex. 4 | Ex. 5 | Ex. 6 | Ex. 7 |
| Water | 76.05 | 71.05 | 63.55 | 58.55 |
| Petrolatum | 12.50 | 17.50 | 25.00 | 30.00 |
| Cyclomethicone (silicone) | 5.00 | 5.00 | 5.00 | 5.00 |
| Aluminum starch octenylsuccinate (starch) | 3.00 | 3.00 | 3.00 | 3.00 |
| Steareth-2 (emulsifier) | 1.73 | 1.73 | 1.73 | 1.73 |
| Steareth-20 (emulsifier) | 0.58 | 0.58 | 0.58 | 0.58 |
| Imidazolidinyl urea (preservative) | 0.30 | 0.30 | 0.30 | 0.30 |
| Methylparaben (preservative) | 0.20 | 0.20 | 0.20 | 0.20 |
| Propylparaben (preservative) | 0.15 | 0.15 | 0.15 | 0.15 |
| Carbomer 941 (stabilizer) | 0.12 | 0.12 | 0.12 | 0.12 |
| Triethanolamine (neutralizing agent) | 0.12 | 0.12 | 0.12 | 0.12 |
| Mixture of sodium cetyl-stearyl sulfate (co-emulsifying agent) | 0.10 | 0.10 | 0.10 | 0.10 |
| Cetyl alcohol (viscosity adjuster) | 0.10 | 0.10 | 0.10 | 0.10 |
| Disodium EDTA (stabilizer) | 0.05 | 0.05 | 0.05 | 0.05 |

| Foam-producing aerosol composition | |
|---|---|
| A - Ingredients | % by weight |
| Aerosol emulsion concentrate (Examples 4 and 5) | 95% |
| Propellant blend (60% difluoroethane - 40% butane) | 5% |
| B - Ingredients | % by weight |
| Aerosol emulsion concentrate (Examples 6 and 7) | 93% |
| Propellant blend (80% isobutane 20% propane) | 7% |

What is claimed is:

1. A skin conditioning composition for application to the skin comprising an oil-in-water emulsion and a propellant packaged under pressure in an aerosol device under such conditions so as to form a foam having a foam density which changes less than 30 percent from initial dispensing to final dispensing from said aerosol device, said oil-in-water emulsion comprising at least 10 percent by weight of petrolatum, at least 50 weight percent of water, an emulsifier having a Hydrophile-Lipophile Balance value of 6 to 10 and a starch or modified starch ester, said propellant (1) being at least one of a hydrocarbon or a fluorocarbon, or a combination thereof, (2) having a vapor pressure within the range of about 5 to about 200 pounds per square inch gauge at 70° F. and (3) being present in an amount such that the density of the foam produced on dispensing said composition ranges between about 0.02 to about 0.20 gram/cc.

2. The skin conditioning composition of claim 1, wherein said starch is a hydrophobic starch.

3. The skin conditioning composition of claim 2, wherein said hydrophobic starch is an aluminum starch octenylsuccinate.

4. The skin conditioning composition of claim 1, wherein said oil-in-water emulsion also contains a volatile silicone.

5. The skin conditioning compoisition of claim 4, wherein said volatile silicone is cyclomethicone.

6. The skin conditioning composition of claim 1, wherein said emulsifier has Hydrophile-Lipophile Balance value of 7 to 9.

7. The skin conditioning composition of claim 1, wherein said emulsifier has a Hydrophile-Lipophile Balance of about 8.

8. The skin conditioning composition of claim 1, wherein said emulsifier is a blend of emulsifying agents.

9. The skin conditioning composition of claim 1, wherein said emulsifier comprises an ethoxylated fatty alcohol.

10. The skin conditioning composition of claim 9, wherein said ethoxylated fatty alcohol comprises a polyethylene glycol moiety having an average number of ethylene oxide units between 2 and 20.

11. The skin conditioning composition of claim 10, wherein said ethoxylated fatty alcohol comprises a cetyl-, lauryl-, myristyl-, oleyl-, stearyl-, or tridecyl-alcohol moiety.

12. The skin conditioning composition of claim 11, wherein said emulsifier comprises at least one of steareth-2 or steareth-20, or a combination thereof.

13. The skin conditioning composition of claim 1, which also includes at least one of a stabilizing agent, a neutralizing agent, a viscosity adjuster, a preservative or a fragance.

14. The skin conditioning composition of claim 1, wherein said oil-in-water emulsion comprises about 20% by weight of petrolatum, about 68% by weight of water, about 2.5% by weight of a mixture of steareth-2 and steareth-20, about 5% by weight of cyclomethicone, and about 3% by weight of an aluminum starch octenylsuccinate.

15. The skin conditioning composition of claim 1, wherein said propellant comprises at least one of butane, isobutane, difluoroethane, or a combination thereof.

16. The skin conditioning of claim 1 wherein said propellant is present in an amount ranging from 5 percent to about 10 percent by weight based on the total weight of said composition so that the density of the foam produced on dispensing said composition ranges between about 0.05 and 0.15 gram per cc.

17. The skin conditioning composition of claim 1 wherein said propellant has a vapor pressure within the range of about 20 to about 70 pounds per square inch gauge at 70° F.

18. The skin conditioning composition of claim 1 wherein said propellant is a mixture of a straight chain or branched chain or cylic saturated aliphatic hydrocarbon and a saturated, partially fluorinated aliphatic hydrocarbon.

19. The skin conitioning in composition of claim 18 wherein said propellant mixture comprises 60 weight percent difluoroethane and 40 weight percent butane or isobutane.

* * * * *